US008034101B2

(12) United States Patent
Yamamoto et al.

(10) Patent No.: US 8,034,101 B2
(45) Date of Patent: Oct. 11, 2011

(54) MAGNESIUM-BASED BIODEGRADABLE METALLIC MATERIAL

(75) Inventors: Akiko Yamamoto, Tsukuba (JP); Sachiko Hiromoto, Tsukuba (JP); Norio Maruyama, Tsukuba (JP); Toshiji Mukai, Tsukuba (JP); Hidetoshi Somekawa, Tsukuba (JP)

(73) Assignee: National Institute for Materials Science, Ibaraki (JP)

( * ) Notice: Subject to any disclaimer, the term of this patent is extended or adjusted under 35 U.S.C. 154(b) by 58 days.

(21) Appl. No.: 12/085,161

(22) PCT Filed: Nov. 16, 2006

(86) PCT No.: PCT/JP2006/322890

§ 371 (c)(1), (2), (4) Date: Aug. 1, 2008

(87) PCT Pub. No.: WO2007/058276

PCT Pub. Date: May 24, 2007

(65) Prior Publication Data

US 2009/0171452 A1 Jul. 2, 2009

(30) Foreign Application Priority Data

Nov. 16, 2005 (JP) ................................ 2005-331841

(51) Int. Cl.
*A61F 2/82* (2006.01)

(52) U.S. Cl. ...................................... 623/1.38; 422/422

(58) Field of Classification Search ................. 623/1.15, 623/23.75, 1.38; 424/422; 428/34.1

See application file for complete search history.

(56) References Cited

U.S. PATENT DOCUMENTS

| | | | | |
|---|---|---|---|---|
| 6,328,657 | B1 | 12/2001 | Kitagawa et al. | |
| 2002/0004060 | A1 * | 1/2002 | Heublein et al. | 424/422 |
| 2004/0045639 | A1 | 3/2004 | Kikawa et al. | |
| 2008/0017285 | A1 * | 1/2008 | Mukai et al. | 148/667 |
| 2008/0033530 | A1 * | 2/2008 | Zberg et al. | 623/1.15 |

FOREIGN PATENT DOCUMENTS

| | | |
|---|---|---|
| JP | 2001-181772 | 7/2001 |
| JP | 2001181772 A * | 7/2001 |
| JP | 2003-129160 | 5/2003 |
| JP | 2003-166031 | 6/2003 |
| JP | 2004-176180 | 6/2004 |

OTHER PUBLICATIONS

Taiji Nishizawa. Thermodynamics of Microstructures. (Jan. 1, 2008). ASM International Publisher. pp. 160-161.*

Yibin Ren et al. "*Study of Bio-Corrosion of Pure Magnesium*", Acta Metallurgica Sinica, vol. 41, No. 11, pp. 1228-1232 (2005).

* cited by examiner

*Primary Examiner* — Thomas J Sweet
*Assistant Examiner* — Seema Swaminathan
(74) *Attorney, Agent, or Firm* — Wenderoth, Lind & Ponack L.L.P.

(57) ABSTRACT

As a novel biodegradable metallic material the degradation speed of which in vivo can be controlled over a broad scope while achieving desired mechanical properties such as strength, work hardening and ductility without restricting the shape of an implant device, it is intended to provide a magnesium-based biodegradable metallic material which comprises Mg containing Mg as the major composition and having a concentration of inevitable impurities equal to or less than 0.05 atomic %, is free from precipitates or intermetallic compounds, and has an average grain size being regulated to equal to or less than ¼ of the minimum part of the material.

13 Claims, 5 Drawing Sheets

MAGNESIUM-BASED BIODEGRADABLE METALLIC MATERIAL

This application is the U.S. National Stage of International Application No. PCT/JP2006/322890, filed Nov. 16, 2006.

TECHNICAL FIELD

The present invention relates to a magnesium-based biodegradable metallic material, and to an implant device for medical application using the magnesium-based biodegradable metallic material.

More specifically, the present invention relates to a magnesium-based biodegradable metallic material allowing control of the degradation speed thereof after being implanted in the living body, while demonstrating very well maintained balance between strength and ductility, and relates to an implant device for medical application formed of the magnesium-based biodegradable metallic material.

BACKGROUND ART

Conventionally used metal biomedical devices in the medical field are often used for the part of the body that need strength, such as bone and tooth.

The reason is that the metal biomaterials used for such devices have superior mechanical properties to polymeric materials and ceramic materials.

Conventional metallic biomedical devices, such as dental implants, total hip prosthesis, fracture fixation systems, stents, etc. will remain inside of the body until removal thereof by operation etc. after being implanted in the living body, and it is desirable that some of the devices are promptly removed after the restoration of peripheral tissues.

For example, in the case of coronary stents, they become unnecessary after the restoration of damaged vascular tissues by opening of the narrowed area.

However, since the removal needs an open chest surgery and gives large physical, mental, temporal, and financial burden to the patient the coronary stents are left behind inside of the body in most cases.

In such a case, the difference in the mechanical properties between the metallic materials that form the device and the living tissue causes mechanical stimulation at every pulsation of the heart to surrounding vascular tissues of the device, resulting in possible induction of the restinosis by the intimal thickening.

Moreover, removal of the device by reoperation is not often performed in fracture fixation systems. Therefore, metal fixtures having a strength superior to that of the bones will support most of the load and sufficient loads are not applied for the bones, leading to insufficient restoration of the bones.

Under these conditions, biodegradable polymeric or ceramic materials have been proposed.

In some cases, however, the biodegradable polymeric and ceramic materials cannot serve as substitute for metallic biomedical devices in respect of their mechanical properties.

Meanwhile, implant devices composed by biodegradable metallic materials in the living body have been proposed (for example, refer to Patent Documents 1 and 2).

Patent Document 1: PCT National Publication No. 2001-511049

Patent Document 2: Japanese Patent Application Laid-Open No. 2004-160236

DISCLOSURE OF INVENTION

Problem to be Solved by the Invention

However, metallic materials of the above-described Patent Documents 1 and 2 contain magnesium as a major composition, but practically need addition of two or more kinds of alloying elements in order to satisfy their mechanical properties.

And the metallic material of the Patent Document 2 does not take the degradation speed into consideration at all, and thus has a problems of limited application in the living body and, at the same time, of difficulty of design of implant device by use thereof.

In the metallic material of the Patent Document 1, adjustment of the thickness of the material controls the corrosion rate, but the obtained implant device has a problem of limitation of the shape, such as thickness etc. by the corrosion rate.

For example, a smaller thickness of the implant device is needed in order to complete the corrosion in a short period of time, but there occurs a problem of less advantage for making the implant device with metallic materials because of the reduction of the strength by the decrease in the thickness.

That is, the degradation speed is not optimized for the object of the implant device, it has various problems in practical use like metallic material of the Patent Document 2.

Moreover, conventional common magnesium alloys have realized strengthening mainly by utilizing crystallization and precipitation of coarse intermetallic compounds which is the combination of supersaturated different elements, or by uniformly dispersing precipitates at a high concentration.

However, since such conventional magnesium alloys depends on dispersion strengthening with the intermetallic compounds, they have the inevitable disadvantage of poor ductility.

Use of such magnesium alloys as a magnesium-based biodegradable metallic material allows the remaining of microparticles of intermetallic compounds in the human body, because they have a lower possibility of degradation in the environment such as inside the living body, which leads to the possibility of inducing the inflammatory response of the living body and the obstruction of the peripheral vessels. Furthermore, as the adding concentration of the alloying element becomes higher, there may occur a problem of possible inducement of the toxicity of ions or compounds due to the release of the alloying element, instead of magnesium used as the main composition.

Furthermore, the influences of the elements that have limited experience in their usage by human beings such as rare earth elements have hardly been investigated for the mammals including human beings, that is, their toxicity to the living body is not yet known.

Therefore, the present invention is completed in view of the above-mentioned situation and aims at providing a novel magnesium-based biodegradable metallic material that can solve problems of the conventional technology and can allow control of degradation speed at a wide range in the living body while attaining desired mechanical properties such as strength, work hardening, ductility, etc., without any limitation in the shape of implant devices.

Means for Solving the Problems

In order to solve the above-described problems, a first aspect of the present invention is to provide a magnesium-based biodegradable metallic material including Mg at a concentration of inevitable impurities equal to or less than 0.05 atomic %, which does not contain any precipitate and intermetallic compound and having an average grain size controlled to be equal to or less than ¼ of the minimum part of a structural component.

A second aspect of the present invention is to provide a magnesium-based biodegradable metallic material including: Mg equal to or more than 93.5 atomic % as the main composition; a secondary element having a larger metallic radius than that of the magnesium at a concentration equal to or less than ⅓ of the solubility limit to the magnesium; inevitable impurities as remainders, while its average grain size is controlled to be equal to or less than ¼ of the minimum part of the structural component and the concentration of the secondary element at the grain boundary is controlled unevenly as equal to or more than 1.5 times of an average concentration inside the grain.

The metallic radii of the elements are, for example, described in Guidebook to Chemistry (Kagaku Binran) Basic volume, 5th revised edition (Maruzen, Tokyo 2004) by the Chemical Society of Japan, and the solubility limits to magnesium are, for example, described in Binary Alloy Phase Diagrams Second edition, Plus Updates Version 1.0 (ASM International, 1996).

A third aspect of the present invention is to provide the magnesium-based biodegradable metallic material described above, wherein the secondary composition is included at a concentration equal to or less than ¼ of the solubility limit to the magnesium.

A fourth aspect of the present invention is to provide the magnesium-based biodegradable metallic material described above, wherein the secondary composition includes any one element among Au, Ir, Pd, Mn, Zr, Bi, Co, Zn, Pu, Ga, Ag, Al, and Li.

A fifth aspect of the present invention is to provide a magnesium-based biodegradable metallic material including: Mg equal to or more than 93.5 atomic % as a main composition; and a secondary element having a smaller metallic radius than that of the magnesium at a concentration equal to or less than ⅓ of the solubility limit to the magnesium; inevitable impurities as remainders, while its average grain size is controlled to be equal to or less than ¼ of the minimum part of the structural component and the concentration of the secondary element at the grain boundary is controlled unevenly as equal to or more than 1.2 times of an average concentration inside the grain.

The metallic radii of the elements are, for example, described in Guidebook to Chemistry (Kagaku Binran) Basic volume, 5th revised edition (Maruzen, Tokyo 2004) by the Chemical Society of Japan, and the solubility limits to magnesium are, for example, described in Binary Alloy Phase Diagrams Second edition. Plus Updates Version 1.0 (ASM International, 1996).

A sixth aspect of the present invention is to provide the magnesium-based biodegradable metallic material described above, wherein the secondary composition is included at a concentration equal to or less than ¼ of the solubility limit to the magnesium.

A seventh aspect of the present invention is to provide the magnesium-based biodegradable metallic material described above, wherein the secondary composition includes any one element among Ce, Pr, La, Th, Nd, Ca, Yb, Rb, Y, Gd, Dy, Ho, Tm, Er, Lu, Sc, and In.

An eighth aspect of the present invention is to provide an implant device for medical application, wherein at least a part of the device is formed of any one of the magnesium-based biodegradable metallic materials described above.

A ninth aspect of the present invention is to provide an implant device for medical application, wherein a structural component having a shape of a pipe or a pipe-like shape is formed with the magnesium-based biodegradable metallic material.

A tenth aspect of the present invention is to provide an implant device for medical application, wherein the device is a coil, a shield, a stent, a wire knitted fabric, a clip, or a plug.

An eleventh aspect of the present invention is to provide an implant device for medical application, which completes its degradation in the living body within a period of 5 days to 6 months after being implanted.

A twelfth aspect of the present invention is to provide an implant device, which completes its degradation in the living body within a period of 1 week to 12 weeks after being implanted.

A thirteenth aspect of the present invention is to provide an implant device for medical application specific for orthopedics.

A fourteenth aspect of the present invention is to provide an implant device for medical application, which completes its degradation in the living body within a period of 6 months to 5 years after being implanted.

A fifteenth aspect of the present invention is to provide an implant device for medical application, which completes its degradation in the living body in a period of 8 months to 3 years after being implanted.

BEST MODE FOR CARRYING OUT THE INVENTION

Figure 1:
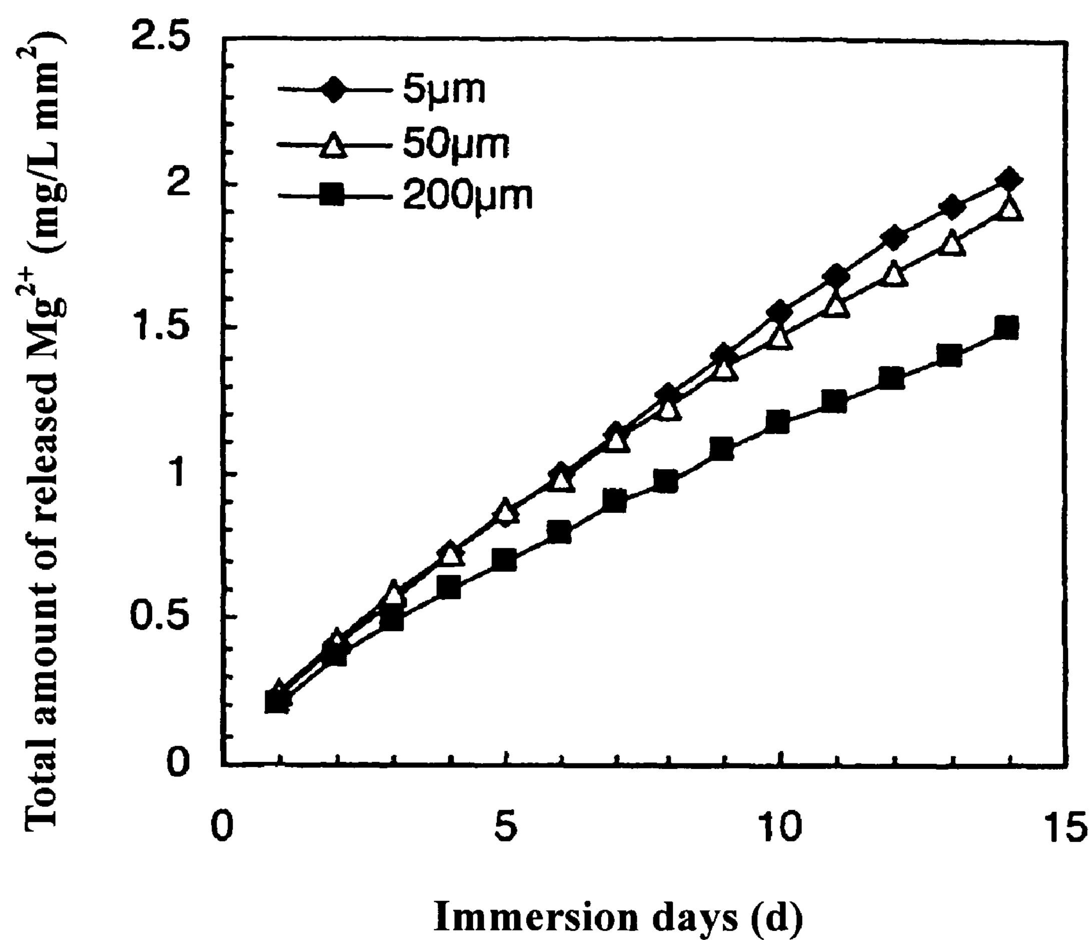
FIG. 1 is a graph illustrating the degradation speeds of pure magnesium having different grain sizes in a cell culture medium.

The present invention has advantages as described above, and a mode for carrying out the present invention will be described hereinafter.

The magnesium-based biodegradable metallic material according to the present invention is a magnesium alloy including: Mg (magnesium) having inevitable impurities equal to or less than 0.05 atomic %, or Mg equal to or more than 93.5 atomic % as the main composition, in which the average grain size is controlled to be equal to or less than ¼ of the minimum part of the structural component.

This magnesium is one of the essential elements for the living body, and is contained in a human body at a proportion of approximately 1.5 g/kg body weight.

Hypermagnesium symptoms due to oral administration have not been confirmed, that is magnesium is an element having low adverse effect of the living body. Generation of magnesium ion and degradation compounds by degradation in the living body has a very low possibility to cause adverse effect.

Since it has inferior corrosion resistance, it may corrode in aqueous solutions containing salts etc. like body fluids. Therefore, the biodegradable metallic materials described in the present invention, which is almost as same as pure magnesium is now under development to be used as biodegradable metallic materials for medical application.

However, simple pure magnesium does not have sufficient mechanical properties for some devices to be manufactured.

Since they are used as what is called structural materials for the living bodies, the devices substituting for bones etc. that support loads especially need not only a higher tensile strength but higher ductility as well.

Simultaneously, it needs to enable controlling its degradation speed in order to support a load during a desired period of time in the living body.

For this reason, the biodegradable metallic materials for medical application of the present invention can secure mechanical properties, such as a strength-ductility balance as well as allowing the control of their degradation speeds in the living body by alloying with addition of other elements, by refinement of the grain size of the microstructure, and by controlling the concentration of the secondary composition unevenly distributed at the grain boundary.

The average grain size of the magnesium-based biodegradable metallic material of the present invention is controlled to be in a range equal to or less than ¼ of the minimum part of the structural component.

Variation of the grain size of magnesium and its alloys thereof varies the mechanical property, degradation speed, etc. The value of the mechanical properties of the magnesium-based biodegradable metallic materials having different grain sizes in Table 1 clearly shows the effect of the grain refinement giving a higher tensile strength.

Moreover, smaller grain sizes increase the grain boundary that has effects on corrosion resistance, therefore it shows a tendency to increase the degradation speed. Values of the degradation speed of the magnesium-based biodegradable metallic materials having different grain sizes in FIG. 1 and Table 3 clearly show a tendency to increase the degradation speed by grain refinement upto 5 μm. The 1-μm has a lower degradation speed than that of the 5-μm material. This is probably because a grain size smaller than a certain threshold enlarges the range influenced by the grain boundary to cover all the are of the grain, resulting in uniform sample in a whole area.

As described above, the control of the grain size enables to control the mechanical property and degradation speed of the magnesium-based biodegradable material.

In the case of smaller devices, such as stents, they have a thickness of only hundreds of μm, and excessively large grain size decreases the number of grains per section. Then, the anisotropic mechanical property of each grain will be reflected to the strength property of structural components, and as a result, the deformation of a grain with the lowest strength to a load-working direction defines the strength of the device. However, as the number of the grains per section increases, the property of each grain is balanced to each other, giving an equalized mechanical properties.

Taking these facts into consideration, an excessively large grain size is not preferred for application to fine structural components. As the thickness of a stent has a thickness of approximately 200 μm, the maximum value of the possible grain size is probably equal to or less than 50 μm. Since the thickness of mini- or micro-plate system is about 0.8 to 4 mm, the maximum value of the possible grain size is probably equal to or less than 200 μm.

The magnesium alloy in the magnesium-based biodegradable metallic material of the present invention includes one element as the secondary composition at a concentration equal to or less than ⅓ of the solubility limit to magnesium. Even in this case, it goes without saying that inevitable impurities is allowed, for example, equal to or less than 0.05 atomic %.

The above-described secondary composition is more preferably included at a concentration equal to or less than ¼ of the solubility limit of the element to magnesium.

And the above-described secondary composition is more preferred to be any one element among Au, Ir, Pd, Mn, Zr, Bi, Co, Zn, Pu, Ga, Ag, Al, Li, Ce, Pr, La, Th, Nd, Ca, Yb, Rb, Y, Gd, Dy, Ho, Tm, Er, Lu, Sc, or In, excluding the elements hardly dissolve in magnesium and the elements clearly having adverse effect on the living body.

Secondary composition will be described in more detail as follows: Ce equal to or less than 0.03 atomic %, Pr equal to or less than 0.03 atomic %, Au equal to or less than 0.033 atomic %, Ir equal to or less than 0.043 atomic %, La equal to or less than 0.047 atomic %, Pd equal to or less than 0.067 atomic %, Th equal to or less than 0.17 atomic %, Nd equal to or less than 0.21 atomic %, Ca equal to or less than 0.3 atomic %, Mn equal to or less than 0.3 atomic %, Zr equal to or less than 0.35 atomic %, Bi equal to or less than 0.37 atomic %, Yb equal to or less than 0.4 atomic %, Rb equal to or less than 0.47 atomic %, Co equal to or less than 0.64 atomic %, Zn equal to or less than 0.8 atomic %, Pu equal to or less than 0.8 atomic %, Ga equal to or less than 1.0 atomic %, Y equal to or less than 1.3 atomic %, Ag equal to or less than 1.3 atomic %, Gd equal to or less than 1.5 atomic %, Dy equal to or less than 1.6 atomic %, Ho equal to or less than 1.8 atomic %, Tm equal to or less than 2.1 atomic %, Er equal to or less than 2.4 atomic %, Lu equal to or less than 3.0 atomic %, Al equal to or less than 3.9 atomic %, Sc equal to or less than 5.0 atomic %, Li equal to or less than 5.7 atomic %, and In equal to or less than 6.5 atomic %.

More preferably, they are: Ce equal to or less than 0.023 atomic %, Pr equal to or less than 0.023 atomic %, Au equal to or less than 0.025 atomic %, Ir equal to or less than 0.033 atomic %, La equal to or less than 0.035 atomic %, Pd equal to or less than 0.05 atomic %, Th equal to or less than 0.13 atomic %, Nd equal to or less than 0.16 atomic %, Ca equal to or less than 0.23 atomic %, Mn equal to or less than 0.23 atomic %, Zr equal to or less than 0.26 atomic %, Bi equal to or less than 0.28 atomic %, Yb equal to or less than 0.3 atomic %, Rb equal to or less than 0.35 atomic %, Co equal to or less than 0.48 atomic %, Zn equal to or less than 0.6 atomic %, Pu equal to or less than 0.6 atomic %, Ga equal to or less than 0.79 atomic %, Y equal to or less than 0.94 atomic %, Ag equal to or less than 0.96 atomic %, Gd equal to or less than 1.1 atomic %, Dy equal to or less than 1.2 atomic %, Ho equal to or less than 1.4 atomic %, Tm equal to or less than 1.6 atomic %, Er equal to or less than 1.8 atomic %, Lu equal to or less than 2.3 atomic %, Al equal to or less than 3.0 atomic %, Sc equal to or less than 3.8 atomic %, Li equal to or less than 4.3 atomic %, and In equal to or less than 4.9 atomic %.

Conventional common magnesium alloys mainly realize strengthening mainly by utilizing crystallization and precipitation of coarser intermetallic compounds which is the combination of supersaturated different elements, or by uniformly dispersing precipitates at a high concentration.

However, since such conventional magnesium alloys depends on dispersion strengthening with intermetallic compounds, they have the inevitable disadvantage of poor ductility.

Use of such magnesium alloys as a magnesium-based biodegradable metallic material allows the remaining of microparticles of the intermetallic compounds in the human body, because they have a lower possibility of degradation in the environment such as inside the living body, which leads to the possibility to cause inflammation in the living body and the obstruction of the peripheral vessels. Furthermore, as the adding concentration of the alloying element become higher, there may occur a problem of possible inducement of the toxicity of ions or compounds due to the release of the alloying elements instead of magnesium used as the main composition.

The influences of the elements the have limited experience in their usage by human beings such as rare earth elements have hardly been investigated for the mammals including human beings, that is, their toxicity against the living body is not yet known.

In general, the toxicity of elementary compounds for the living body depends on their concentrations (amounts) in the living body. When the element is not an essential element, less amount of the element reduces the possibility of the appearance of their toxicity.

Therefore, for the magnesium-based biodegradable metallic material of the present invention, only the elements that have lower toxicity for the living body are firstly selected as a secondary composition, and moreover, the concentration of the secondary element is not set unnecessarily higher to secure the function as a magnesium-based biodegradable metallic material without having any precipitates and intermetallic compounds.

The limited range of the concentration of these secondary composition is set in a range upto approximately ⅓ of the solubility limit to magnesium, and desirably in a range equal to or less than approximately ¼ for the elements included in groups 2, 3, 4, 5, and 6 or lanthanoids in the periodic table excluding those having distinct toxicity for the living body.

It has been found out that the secondary composition of the magnesium alloys have two kinds of elements having a metallic radius smaller or larger than that of Mg, and they have functions different from each other.

Inclusion of any elements among them at a certain concentration equal to or less than ⅓ of the solubility limit to magnesium, more preferably equal to or less than ¼, can increase the yield strength and the tensile strength, without impairing fundamental functions as biodegradable metallic materials for medical application.

It has been found out that, however, that addition of one element among Ce, Pr, La, Th, Rb, Ho, Tm, Er, Lu, Nd, Ca, Yb, Y, Gd, Dy, Sc, and In having a larger metallic radius than that of Mg lowers the stationary degradation speed rather than the addition of an element among Au, Ir, Pd, Mn, Co, Ga, Ag, Al, Zn, Zr, Bi, Pu, and Li having smaller metallic radius.

That is, the present invention elucidates that the corrosion resistance of the magnesium-based biodegradable metallic material may be controlled by the kinds and amounts of secondary elements to be added.

Furthermore, in the present invention, it has been confirmed that the control of the average grain size as described above is possible for these compositions.

In addition, the elements having distinct toxicity for the living body are those having the 50% lethal dose of 300 mg/kg or less by oral administration to animals which described in Poisonous and Deleterious Substances Control Law as control criteria, by "50% lethal dose to rat of metals and metallic compounds by oral administration ($LD_{50}$)" (Akiko Yamamoto Materia Japan 43 (8), 639-642, 2004), or toxic elements described in "Why human body needs metals" (by Hiromu Sakurai, Kodansha, 1996).

Furthermore, the above-described secondary composition also includes Th and Pu; their major isotopes are radioactive elements. The is because the investigations of utilizing radioisotopes for the treatment of tumors have been performed in recent years, suggesting the possible application of the biodegradable metallic materials of the present invention for such an object.

Since the range of the concentrations of these secondary compositions is that hardly inducing precipitations, fractures do not easily progress, at the interface of the precipitates, etc., leading to have higher ductility.

Simultaneously, the concentration of the added element can be limited to a relatively low concentration, leading to suppress the risk of inducing the toxicity of the added element for the living body.

In addition, the selection of the secondary composition has great influence on the mechanical properties, degradation speeds, etc. of the magnesium-based biodegradable metallic material to be obtained.

As shown in Table 1, even though they have the same average grain size of 1 μm, the alloys containing the secondary constituent elements at 0.3 atomic % have better mechanical properties than that of pure magnesium, showing clear effect of alloying. Furthermore, it is also clearly shown that the kinds of the secondary constituent element provide different level of the improvement of their mechanical properties. For example, in the case of the average grain size of 1 μm, magnesium alloy containing Ca at 0.3 atomic % has a higher strength than that of magnesium alloy containing Li at 0.3 atomic %.

Concerning the degradation speed as shown in Table 3, even though they have the same average grain size of 1 μm, the alloys containing the secondary constituent elements at 0.3 atomic % have a smaller steady-stage degradation speeds than that of pure magnesium, showing clear effect of alloying. Furthermore, it is also clearly shown that the kinds of the secondary constituent element provide different level of the decrease of their steady-state degradation speeds. For example, in the case of the average grain size of 1 μm, magnesium alloy containing Ca at 0.3 atomic % has a lower steady-state degradation speed than that of magnesium alloy containing Li at 0.3 atomic %. In the case of the alloys containing the secondary constituent elements at 0.3 atomic %, the alloys containing the elements having larger metallic radii tend to have lower steady-state degradation speeds comparing to the alloys containing the elements having smaller metallic radii than that of Mg. However, since each element of the secondary composition has a different relationship with magnesium and environments in the living body, these tendencies are not strictly accepted but will be a general guideline.

Variation of the concentration of the secondary constituent element can also vary the degradation speed of the alloy. Table 3 and FIG. 3 clearly show that the steady-state degradation speeds of the alloys having an average grain size of approximately 1 μm and containing Al or Li at a concentration of 0.3, 0.6, or 1.0 atomic % are varied with the concentration of the secondary constituent elements.

Thus, even though they have the same average grains size, the selection of the secondary composition and the control of its concentration can vary the strength and the degradation speed of the alloy, therefore, it will be possible to obtain a magnesium-based biodegradable metallic material having the desired balance of both the strength and the degradation speed.

The mechanical properties and degradation speed of the magnesium-based biodegradable metallic materials of the present invention are deeply related with the variation of the concentration of the secondary constituent element unevenly distributed at the grain boundary as the results of controlling the average grain size, the kinds and the concentrations of the secondary constituent element. It is considered that uneven distribution of the secondary constituent element at the grain boundary enhances the grain boundary, which contributes to strengthen and to reduce the degradation speeds of the magnesium alloys. For example, in detail, the magnesium alloys of the present invention are controlled to have the concentration of the secondary composition unevenly distributed at the grain boundary as equal to or more than 1.5 times of an average concentration within the grain.

The difference between the concentration of the secondary composition unevenly distributed at the grain boundary and the average concentration within the grain varies with the grain size of the alloy, the kind and the concentration of the secondary constituent element. The maximum concentration of the secondary constituent element at the grain boundary is the solubility limit of the element to magnesium. Therefore, when the concentration of the secondary constituent element is equal to its solubility limit, the concentration of the secondary component at the grain boundary is, ideally (having no precipitates), equal to the average concentration within the grain (in this case, its solubility limit), resulting in no uneven distribution. Accordingly, the concentration of the secondary composition closer to its solubility limit will give smaller difference between the concentration of the secondary composition unevenly distributed at the grain and the average concentration within the grain.

On the other hand, the smaller grain size gives a larger number of the grain boundaries, leading to higher possibility of the uneven distribution of the secondary constituent element at the grain boundary. In the case of larger grain sizes, that is, in order to have grain growth, it is necessary to keep the material at higher temperatures, leading to enhance the diffusion of substance within the material, which results in less uneven distribution of the secondary constituent element at the grain boundary. Accordingly, materials having a larger grain size will have smaller difference between the concentration of the secondary composition unevenly distributed at the grain boundary and the average concentration within the grain.

Since the properties of the element, such as the size, weight, etc., vary according to the kind of the secondary constituent element, the diffusion rate in the magnesium alloys will vary, providing the variation in the level of uneven distribution at the grain boundary.

As described above, the difference between the concentration of the secondary constituent element unevenly distributed at the grain boundary and the average concentration within the grain will be determined by the combination of the grain size of the magnesium alloys, the kind of the secondary constituent elements, and the concentration of the secondary constituent elements. It is not controllable only by the independent factor of the three.

The difference between the concentration of the secondary constituent element unevenly distributed at the grain boundary and the average concentration within the grain influences the mechanical properties (strength-ductility balance) of the magnesium alloys and their degradation speeds in the living body.

Table 4 illustrates the difference between the concentration of the secondary constituent element unevenly distributed at the grain boundary and the average concentration within the grain in the magnesium-based biodegradable metallic materials of the present invention. It is clearly shown that the alloys containing the same amount of the secondary composition at 0.3 atomic % have variable differences between the concentration unevenly distributed at the grain boundary and the average concentration within the grain, depending on the kind and the concentration of the secondary constituent elements.

Control of the average grain size is attained, for example, by utilizing the microstructure control by work processes.

The control of the grain size is possible by severe plastic deformation such as extrusion and rolling processing at a temperature equal to or more than that inducing recrystallization of the material.

Depending on the composition of the master alloy, an example of the process is that after the homogenization at a temperature in a range of approximately 450 to 550° C. for approximately 1.5 to 8 hours, followed by the quenching to freeze the uniformly dispersed structure, and then a warm strain is applied at a temperature in a range of approximately 80 to 350° C.

The method of controlling the average grain size is not limited to such extrusion and rolling processes, but in the case that the extrusion or rolling process is used, the severe working at a temperature equal to or more than the recrystallizing temperature is indispensable as described above.

A suitable example of the extrusion ratio (cross section ratio) in this case is approximately 16 to 100, that is to be severe working rather than the normal extrusion.

In the magnesium-based biodegradable metallic material of the present invention, the control of the solid solution state of the secondary component to the magnesium and its uneven distribution at the grain boundary can control the strength-ductility balance and the degradation speed as a desired value.

The control of the solid solution state of the secondary component and its uneven distribution at the grain boundary is attained by utilizing the control of the microstructure by processing as well as by the selection of the above-described compositions.

The control of the solid solution state of the secondary component and its uneven distribution at the grain boundary is possible by adjusting the concentration of the secondary component and the grain size.

Implant devices for medical application according to the present invention are characterized in that at least a part thereof comprises the above-described magnesium-based biodegradable metallic material.

Various devices can be used as implant devices for medical application.

Pipe-shaped or pipe-like structural components can be used as fundamental implant devices.

The implant devices can be a coil, a shield, a stent, a wire knitted fabric, a clip, a plug etc.

The degradation speed (a period until degradation is completed after being implanted into the living body) of these implant device for medical applications is controllable by adjusting the composition and the grain size, that is, the kind, the amount, and the uneven distribution of the secondary component.

The range of the control can be in five days to several years as a maximum, and it can be set to one week to twelve weeks after being implanted according to usages.

Furthermore, the implant device for medical application according to the present invention provides a high-tensile strength and high ductility; therefore it can also be used as implants for orthopedics.

In this case, for example, the grain size, the selection of the secondary component and its uneven distribution can be controlled so as to complete the degradation in the living body from six months to five years after being implanted.

More specifically, for example, the degradation in the living body may be controlled to complete in eight months to three years after embedding.

Since the biodegradable metallic material of the present invention can provide broader degradation speeds, the whole degradation period of the above-mentioned implant device for medical application can be set in consideration of the degradation speed per unit volume or unit area, etc., although it cannot be mentioned in general as it also depends on the sizes and shapes.

Since the biodegradable metallic material of the present invention is made of pure magnesium or of a binary alloy of the magnesium, finer control of such the degradation speed can be more simply and precisely performed.

Hereinafter, the mode for carrying out this invention will be described in more detail with reference to Examples.

Of course, the present invention is not limited to the following examples, and various aspects are possible in its details.

EXAMPLE 1

Pure magnesium (3N5) was subjected to severe working by extrusion (extrusion ratio 18) at 94, 180, 268° C., respectively, to adjust the average grain size to 5, 50, and 200 μm. The top, bottom, and the side surface of these specimens (oval shaped, approximately 4 mm in width, 14 mm in length, and 2 mm in thickness) was polished up to No. 600 of a waterproof polishing paper with ethanol, and then, washed with acetone and sterilized. In a 5% $CO_2$ incubator maintained at 37° C., the specimens were immersed for 14 days in a cell culture medium (E-MEM+10% FBS) of 27.5 mL, using a sterilized glass bottle, and then quantitative analysis of the magnesium ion released into the culture medium was performed by the Xylidyl Blue method.

A 15 mL portion of the culture medium was replaced every day, and the collected portion was used for the quantitative analysis of the magnesium ion.

The environment of 37° C. and 5% $CO_2$ is close to the condition inside the human body, and the used cell culture medium (serum added) is the solution having a composition similar to that of the plasma. The tissue fluid (intercellular liquid) is considered as the portion of the plasma permeated from the blood vessel, and the component has a composition similar to that of the plasma.

The amount of the plasma per adult is approximately 2.75 L, and 1.5 L out of the plasma is excreted as urine per day. The amount of the culture medium used for immersion was set to 1/100 scale in case of adult. Since the bottom of the specimen used touches the bottom of the glass bottle, only the upper and the side surface was used for calculation for the surface area of the specimen contacting with the culture medium.

FIG. 1 illustrates the total amount of the released magnesium ion during the immersion period of 14 days. The values shown in the figure are averages of the immersion tests of three samples for one alloy.

It was confirmed that pure magnesium having a smaller grain size released a larger amount of the magnesium into the solution, that is, had a larger degradation speed.

EXAMPLE 2

Pure magnesium (3N5) and eight kinds of the magnesium alloys containing 0.3 atomic % of Al, Ca, Y, Li, Dy, In, Gd, or Zn were subjected to the severe working by extrusion at 90, 160, 240, 310, 85, 275, 140 and 185° C., respectively, (extrusion ratio 18 for pure magnesium and the alloys containing Zn; and extrusion ratio 25 for other seven kinds of magnesium alloys) to control the average grain size as approximately 1 μm. Tensile tests of these materials were performed and their results were shown in Table 1. Tensile tests of casting materials of the alloys containing Y and Ca at 0.3 atomic % (average grain size equal to or more than 100 μm) were performed and their results were also shown in Table 1.

For comparison, Table 2 illustrates mechanical properties of existing magnesium alloys described in ASM Specialty Handbook, Magnesium and magnesium alloys, (Materials Park, Ohio, ASM International, 1999), p. 170.

EXAMPLE 3

The results of the measurement for the distribution of the elementary concentration by high resolution observation and nano-EDS of the alloys containing Y, Ca, or Al of 0.3 atomic % prepared under the same conditions as those in Example 2 were shown in Table 3. Uneven distribution was confirmed as follows: the alloy containing Y gave 0.9 atomic % in the vicinity of the grain boundary, that is, 3 times of the average concentration 0.3 atomic % within the grain; the alloy containing 0.3 atomic % of Ca gave 0.74 atomic % in the vicinity of the grain boundary, that is, 2.7 times of the average concentration of 0.27 atomic % within the grain; and the alloy containing 0.3 atomic % of Al gave 0.49 atomic % in the vicinity of the grain boundary, that is, 1.4 times of the average concentration of 0.34 atomic % in the grain.

TABLE 1

Mechanical properties of the developed magnesium alloys investigated by tensile tests

| | Added element and amount | Yield strength (MPa) | Tensile strength (MPa) | Fracture elongation (%) |
|---|---|---|---|---|
| Example | 0.3 atomic % Li (1 μm) | 170 | 200 | 20 |
| | 0.3 atomic % In (1 μm) | 183 | 212 | 32 |
| | 0.3 atomic % Zn (5 μm) | 198 | 238 | 26.5 |
| | 0.3 atomic % Al (1 μm) | 270 | 270 | 28 |
| | 0.3 atomic % Gd (1 μm) | 358 | 365 | 7.5 |
| | 0.3 atomic % Dy (1 μm) | 370 | 375 | 10 |
| | 0.3 atomic % Y (1 μm) | 370 | 380 | 12 |
| | 0.3 atomic % Ca (1 μm) | 385 | 410 | 14 |
| | Pure Mg material (1 μm) | 161 | 210 | 17 |
| | Pure Mg material (5 μm) | 141 | 167 | 16 |
| | Pure Mg material (50 μm) | 102 | 126 | 12.6 |
| | Pure Mg material (200 μm) | 78 | 144 | 15 |
| Comparative example | 0.3 atomic % Y* (>100 μm) | 24 | 103 | 16 |
| | 0.3 atomic % Ca* (>100 μm) | 29 | 72 | 9 |

*Cast material (without control of grain size and the uneven distribution of the secondary constituent element at the grain boundary by severe plastic deformation)

TABLE 2

Mechanical properties of existing alloys in comparative example (literature value)

| | ASTM (classification) | Yield strength (MPa) | Tensile strength (MPa) | Elongation (%) |
|---|---|---|---|---|
| Rolled plate material | AZ31B(H24) | 220 | 290 | 15 |
| | HK31A(H24) | 200 | 255 | 9 |
| | HM21A(T8) | 170 | 235 | 11 |
| Extruded bar | AZ10A(F) | 145 | 240 | 10 |
| | AZ31B/C(F) | 200 | 260 | 15 |
| | AZ61A(F) | 230 | 310 | 16 |
| | AZ80A(T5) | 275 | 380 | 7 |
| | HM31A(F) | 230 | 290 | 10 |
| | M1A(F) | 180 | 255 | 12 |
| | ZC71(F) | 340 | 360 | 5 |
| | ZK21A(F) | 195 | 260 | 4 |
| | ZK40A(T5) | 255 | 276 | 4 |
| | ZK60A(T5) | 305 | 365 | 11 |
| Die-cast | AM60A/B(F) | 115 | 205 | 6 |
| | AS21X1 | 130 | 240 | 9 |
| | AS41A(F) | 150 | 220 | 4 |
| | AZ91A/B/D(F) | 150 | 230 | 3 |
| Sand mold, metal mold cast material | AM100A(T61) | 150 | 275 | 1 |
| | AZ63A(T6) | 130 | 275 | 5 |
| | AZ81A(T4) | 83 | 275 | 15 |
| | AZ91C/E(T6) | 145 | 275 | 6 |
| | AZ92A(T6) | 150 | 275 | 3 |
| | EQ21A(T6) | 195 | 235 | 2 |
| | EZ33A(T5) | 110 | 160 | 2 |
| | HK31A(T6) | 105 | 220 | 8 |
| | HZ32A(T5) | 90 | 185 | 4 |
| | K1A(F) | 55 | 180 | 1 |
| | QE22A(T6) | 195 | 260 | 3 |
| | QH21A(T6) | 205 | 275 | 4 |
| | WE43A(T6) | 165 | 250 | 2 |
| | WE54A(T6) | 172 | 250 | 2 |
| | ZC63A(T6) | 125 | 210 | 4 |
| | ZE41A(T5) | 140 | 205 | 3.5 |
| | ZE63A(T6) | 190 | 300 | 10 |
| | ZH62A(T5) | 170 | 240 | 4 |
| | ZK51A(T5) | 165 | 205 | 3.5 |
| | ZK61A(T5) | 185 | 310 | — |
| | ZA61A(T6) | 195 | 310 | 10 |

TABLE 3

The concentration of the secondary constituent element in the vicinity of the grain boundary and its average concentration within the grain in the developed magnesium alloys

| | Concentration at grain boundary (atomic %) | Concentration within the grain (atomic %) | Grain boundary/ within grain |
|---|---|---|---|
| 0.3 atomic % Y (1 μm) | 0.90 | 0.30 | 3 |
| 0.3 atomic % Ca (1 μm) | 0.74 | 0.27 | 2.7 |
| 0.3 atomic % Al (1 μm) | 0.49 | 0.34 | 1.4 |

The magnesium alloys of the present invention were confirmed to satisfy the range of the mechanical properties of the existing materials, or to exhibit higher strength and higher ductility.

EXAMPLE 4

Pure Mg, and seven kinds of magnesium alloys containing Al, Ca, Li, Dy, In, Gd, or Zn at 0.3 atomic % which were prepared on the same conditions as above-described Example 2 to control to have average grain size of approximately 1 μm (approximately 5 μm for the alloy containing Zn), were immersed in a cell culture medium of 27.5 mL for 14 days in a 5% $CO_2$ incubator maintained at 37° C. in the same procedure as that in Example 1. Quantitative analysis of the magnesium ion released into the culture medium was performed by the Xylidyl Blue method. A 15 mL portion of the culture medium was replaced every day, and the collected portion was used for the measurement of the released magnesium ion. The shape of the specimen was an oval shape of approximately 4 mm in width, approximately 14 mm in length, and approximately 2 mm in thickness, or a disk shape of approximately 8 mm in diameter, and approximately 2 mm in thickness. An immersion test was performed for two to three specimens of each alloy, and the average was obtained.

Figure 2:
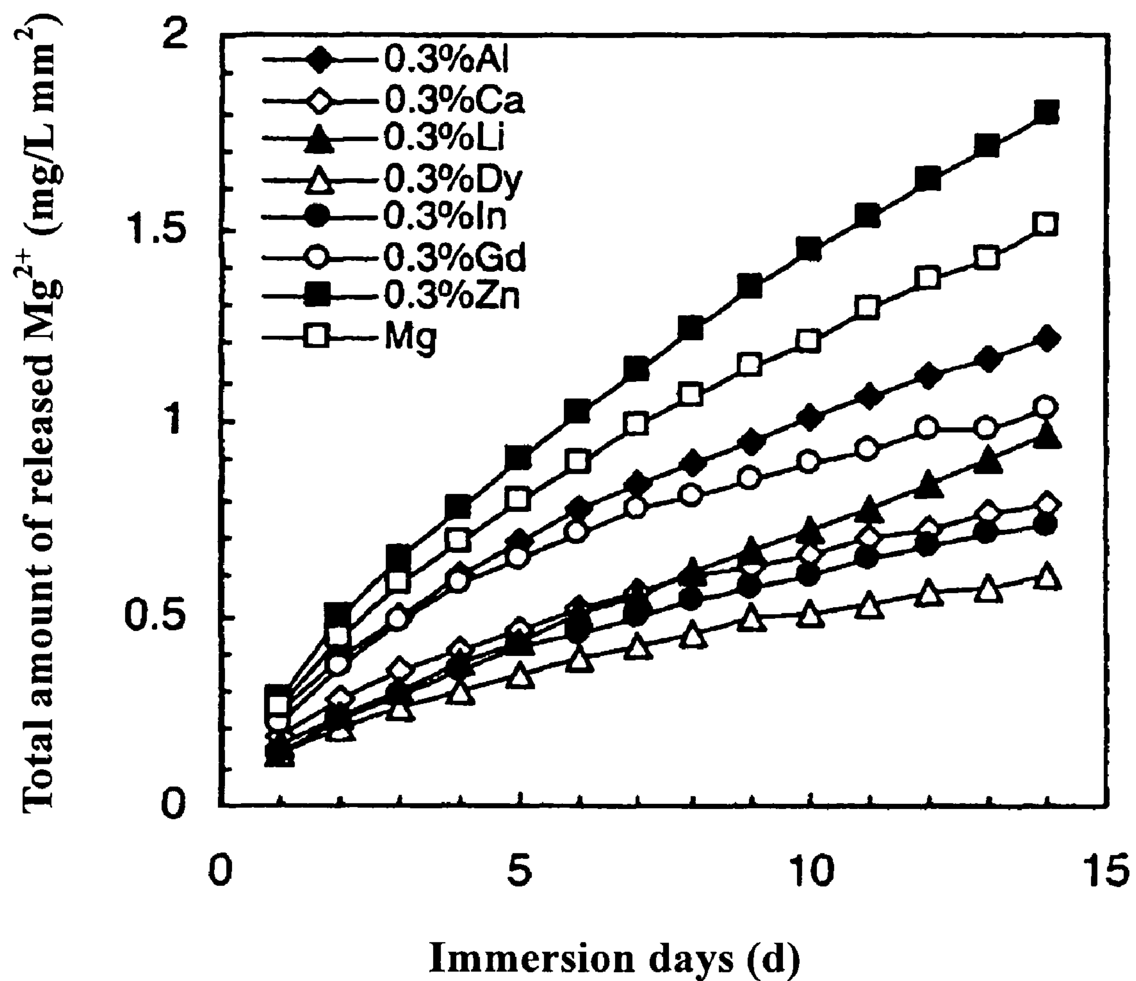
FIG. 2 is a graph illustrating degradation speeds of magnesium alloys having different composition in a cell culture medium.

FIG. 2 illustrates the results.

It was shown that the kind of added element gave a different magnesium amount released into the solution, that is, it could vary the degradation speed.

It was confirmed that addition of Gd, In, Ca, and Dy having a larger metallic radii than that of Mg gave lower steady-state degradation speeds than those in the case of addition of Zn, Al, and Li having a smaller metallic radii.

EXAMPLE 5

Table 4 illustrates the concentration of magnesium ion released on the first day, and average concentrations of the daily release of magnesium ion from the sixth to 14th days for the results of Examples 1 and 4. It can be considered that the former value gives the initial speed of the degradation of the magnesium alloys in the living body, and the latter value gives the degradation speed in a steady state. The latter value was obtained from the gradient of a graph of the total released amount for sixth to the 14th days by the least squares method based on FIGS. 1 and 2.

The results is an average of three specimens and a value in ( ) gives a standard deviation.

Examination of specimens illustrated only in this Table 4 confirms that the control of the grain size, the added element, and the concentration thereof enables the achievement of broader degradation speeds.

For comparison, the immersion test in the same manner was carried out for existing materials. Table 4 illustrates the concentration of magnesium ion released on the first day, and the average concentrations of the daily release of magnesium ion from the sixth to 14th days.

Since the existing materials contain intermetallic compounds at a high volume ratio, the intermetallic compounds that have the low possibility to degrade in the living body environment may remain in the body as microparticles, leading to induce inflammatory reactions of the living body and occlusion of peripheral arteries. The existing materials give the released amount on the first day, that is, the initial degradation speed, a little lower than that of the magnesium alloys of the present invention, and give the released amount on the sixth to 14th days, that is, the steady-state degradation speed of the same grade among the existing materials without any difference.

From these results, it was found out that the magnesium alloys of the present invention can have the steady-state degradation speeds broader than those of the existing materials.

In consideration of the implanting period of the biodegradable devices sometimes being over several years in the living body, the steady-state speed exhibits larger influence on the degradation period of the device than that of the initial speed.

Accordingly, it was confirmed that the control of the composition and the grain size of the developed alloys allows to control their degradation speeds in the living body in a range wider than those of the existing materials.

TABLE 4

The initial degradation speed of various biodegradable magnesium alloys in the cell culture method (release amount on the first day) and steady-state degradation speed (Least square average of the released amount on the sixth to 14th days)

| Material | Initial degradation speed (mg/L and mm$^2$) | Steady-state degradation speed (mg/L and mm$^2$) | Remarks |
|---|---|---|---|
| Pure Mg material (1 μm) | 0.2551 (±0.0319) | 0.0752 (±0.0057) | Example |
| Pure Mg material (5 μm) | 0.2270 (±0.0735) | 0.1312 (±0.0081) | |
| Pure Mg material (50 μm) | 0.2474 (±0.0612) | 0.1175 (±0.0148) | |
| Pure Mg material (200 μm) | 0.2057 (±0.0446) | 0.0870 (±0.0095) | |
| 0.3 atomic % Zn (5 μm) | 0.2835 (±0.0358) | 0.0972 (±0.0084) | |
| 0.3 atomic % Li (1 μm) | 0.1560 (±0.0304) | 0.0586 (±0.0096) | |
| 0.3 atomic % Al (1 μm) | 0.2462 (±0.0640) | 0.0555 (±0.0152) | |
| 0.3 atomic % Gd (1 μm) | 0.1997 (±0.0563) | 0.0391 (±0.0153) | |
| 0.3 atomic % In (1 μm) | 0.1446 (±0.0569) | 0.0344 (±0.0158) | |
| 0.3 atomic % Ca (1 μm) | 0.1881 (±0.0506) | 0.0338 (±0.0161) | |
| 0.3 atomic % Dy (1 μm) | 0.1368 (±0.0359) | 0.0255 (±0.0105) | |
| 0.6 atomic % Li (1 μm) | 0.2678 (±0.0336) | 0.0818 (±0.0146) | |
| 1.0 atomic % Li (7 μm) | 0.2601 (±0.0168) | 0.0623 (±0.0061) | |
| 0.6 atomic % Al (1 μm) | 0.2818 (±0.0273) | 0.0621 (±0.0092) | |
| 1.0 atomic % Al (1 μm) | 0.2769 (±0.0129) | 0.0562 (±0.0045) | |
| 1.0 atomic % Al (5 μm) | 0.4223 (±0.0156) | — | |
| 1.0 atomic % Al (20 μm) | 0.4132 (±0.0217) | — | |
| 0.3 atomic % Y* (>100 μm) | 0.4993 (±0.1025) | — | Comparative |
| 0.3 atomic % Al* (>100 μm) | 0.4410 (±0.0778) | — | example** |
| AM60 (20 μm) | 0.1110 (±0.0083) | 0.0616 (±0.0027) | |
| AZ80 (20 μm) | 0.0869 (±0.0434) | 0.0448 (±0.0073) | |
| WE43 (30 μm) | 0.1056 (±0.0229) | 0.0594 (±0.0102) | |
| WE54 (40 μm) | 0.0688 (±0.0053) | 0.0557 (±0.0102) | |

Average of three specimens, ( ): standard deviation

*Cast material (without the control of grain size and uneven distribution of the secondary constituent element at grain boundary by severe working)

**Each comparative example is commercial extruded material having intermetallic compounds formed at high volume rate

EXAMPLE 6

Of six kinds of magnesium alloys containing 0.3, 0.6, and 1.0 atomic % of Al or Li, each of the alloys containing Al was subjected to the severe working by extrusion at 160, 175, and 210° C. respectively (extrusion ratio 25), and each of the alloys containing Li was subjected to severe working by extrusion at 85, 125, and 125° C. respectively (extrusion ratio 25) to control the average grain size to be approximately 1 μm (approximately 7 μm for the alloy containing 1.0 atomic % of Li).

These specimens were immersed into a cell culture medium of 27.5 mL for 14 days in a 5% $CO_2$ incubator maintained at 37° C. in the same procedure as that in Example 1. Qualitative analysis of the magnesium ion released into the culture medium was performed by the Xylidyl Blue method.

Figure 3:
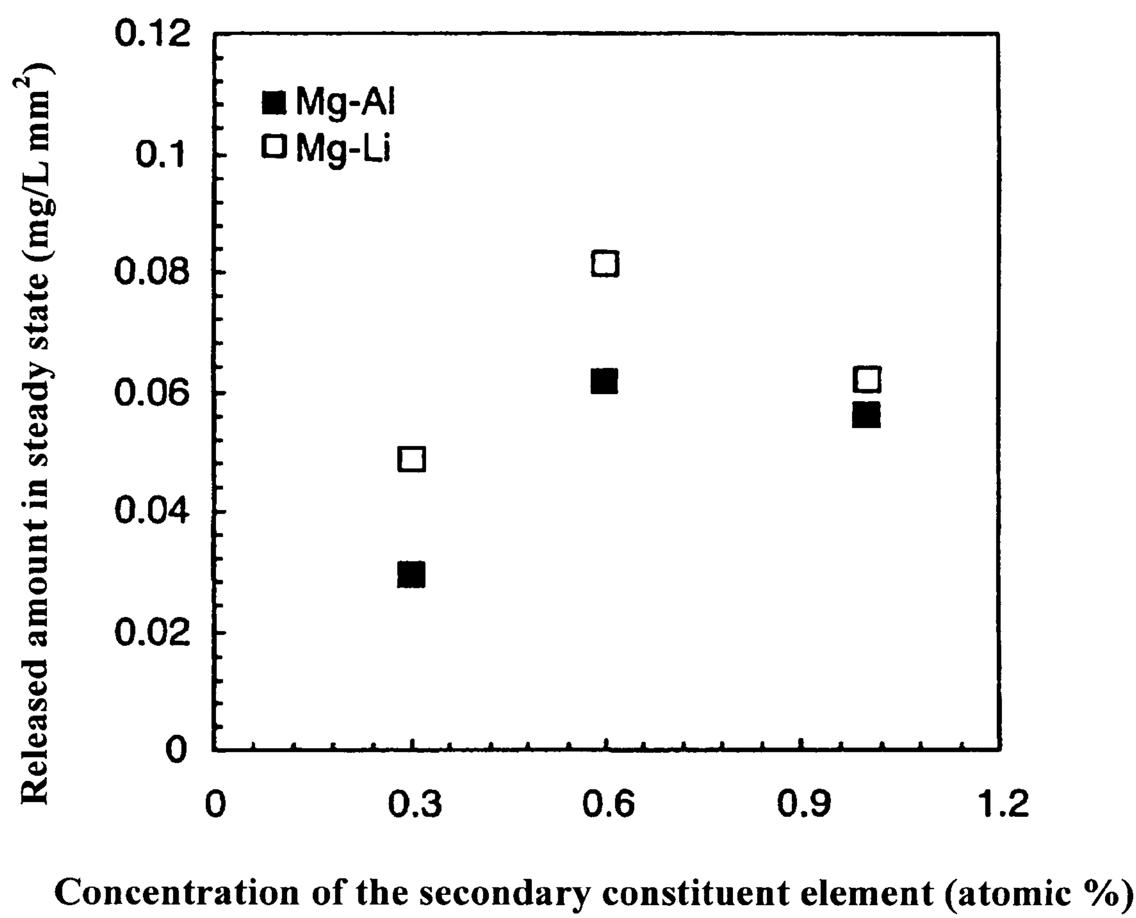
FIG. 3 is a graph illustrating a relationship between a steady-state degradation speed in a cell culture medium and the concentration of the secondary elements for the magnesium alloys having different concentrations of the secondary elements.

Here, a 15 mL portion of the culture medium was replaced every day, and the collected portion was used for the measurement of the magnesium ion. The shape of the specimen was an oval shape of approximately 4 mm in width, approximately 14 mm in length, and approximately 2 mm in thickness, or a disk shape of approximately 8 mm in diameter, and approximately 2 mm in thickness. An immersion test was performed for 2 to 3 specimens of each alloy, and the average was obtained. In the same manner as that of Example 5, were obtained the concentration of magnesium ion released on the first day, and average concentration of the daily release of magnesium ion from the sixth to 14th days. FIG. 3 and Table 4 illustrate these results.

It was shown that the concentration of the added element varies the released amount of magnesium into the solution, that is, it can varies degradation speeds.

EXAMPLE 7

A magnesium alloy containing 1.0 atomic % of Al was subjected to severe working by extrusion (extrusion ratio 25) at 180, 215, and 292° C., respectively, to control their average grain size to be approximately 1, 5, or 10 μm. These specimens and cast materials of alloys containing 0.3 atomic % Al or Y (average grain size equal to or more than 100 μm) were immersed into a cell culture medium of 27.5 mL for 1 day in a 5% $CO_2$ incubator maintained at 37° C. in the same procedure as that in Example 1. Qualitative analysis of the magnesium ion released in the culture medium was performed by the Xylidyl Blue method.

Figure 4:
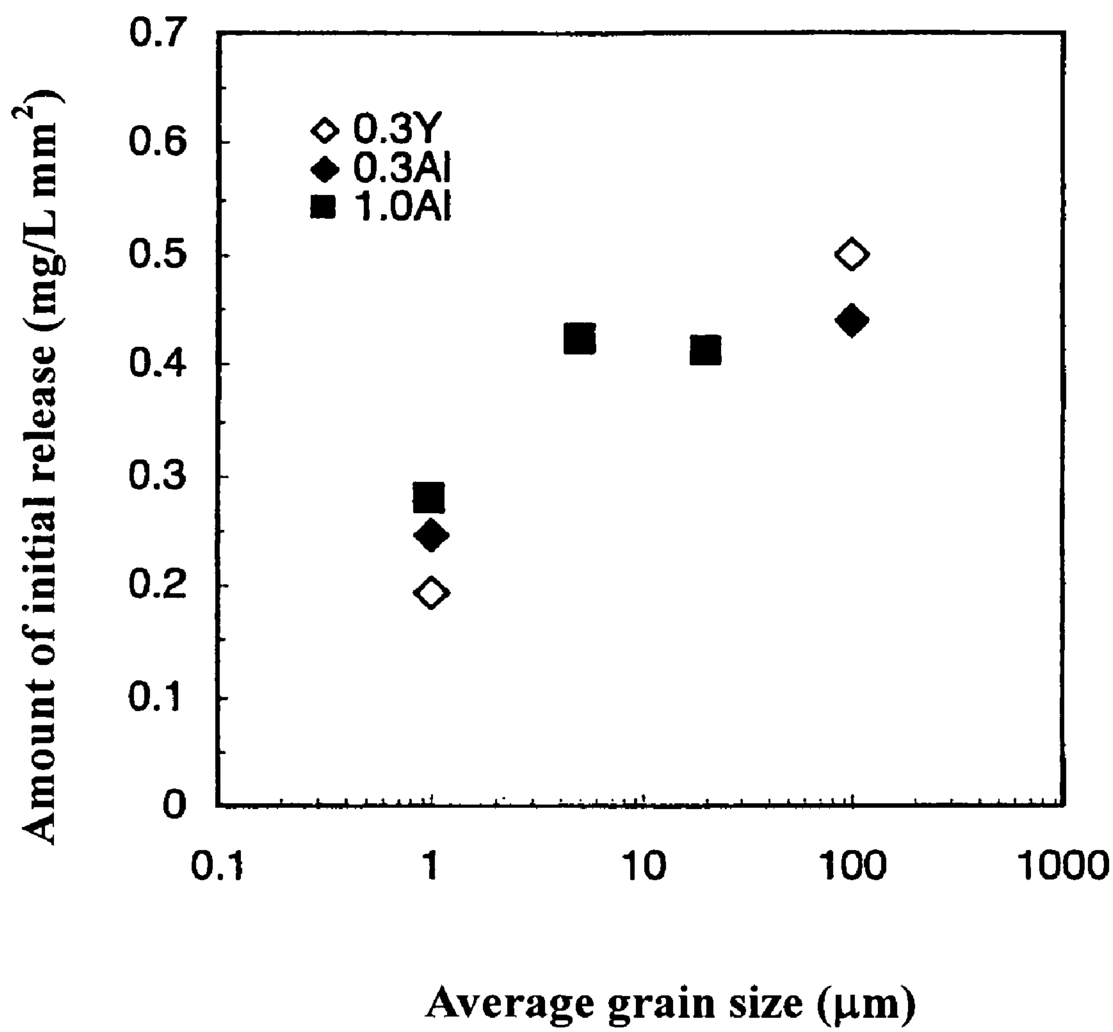
FIG. 4 is a graph illustrating a relationship between an initial degradation speed in a cell culture medium and the concentration of the secondary elements for the magnesium alloys having the same composition but the different average grain sizes.

FIG. 4 illustrates the results of the alloys containing Al, and Table 4 also illustrates the initial degradation speed of all the alloys.

As a result, it was shown that even in the same alloy composition, variation of the grain size can vary the amount of the magnesium released into the solution, that is, it can vary the degradation speed.

EXAMPLE 8

It is dependent on the concentration of the released ion whether the magnesium ion and other metal ions released from the magnesium-based biodegradable metallic material implanted in the body cause damage to the living body or not.

However, it is difficult to estimate since the released amount varies with the shape (size and surface area) of the device.

Therefore, estimation of the amount of released ion was attempted for a stent as an example.

The average size of a stent was assumed to be 3 mm in diameter, 20 mm in length, metal/blood vessel ratio as 15%, 0.15 mm in thickness, and the strut width of 0.1 mm, giving a total surface area as 113 mm$^2$. From the value illustrated in the above-described Table 4, the initial degradation speed of this stent is 25.67 mg/L when it was made by the pure magnesium having the average grain size of 5 μm that gave the largest degradation speed. In the case of the alloy containing 0.3 atomic % of Dy that had the smallest degradation speed, the initial degradation speed of the stent will be 15.46 mg/L.

Figure 5:
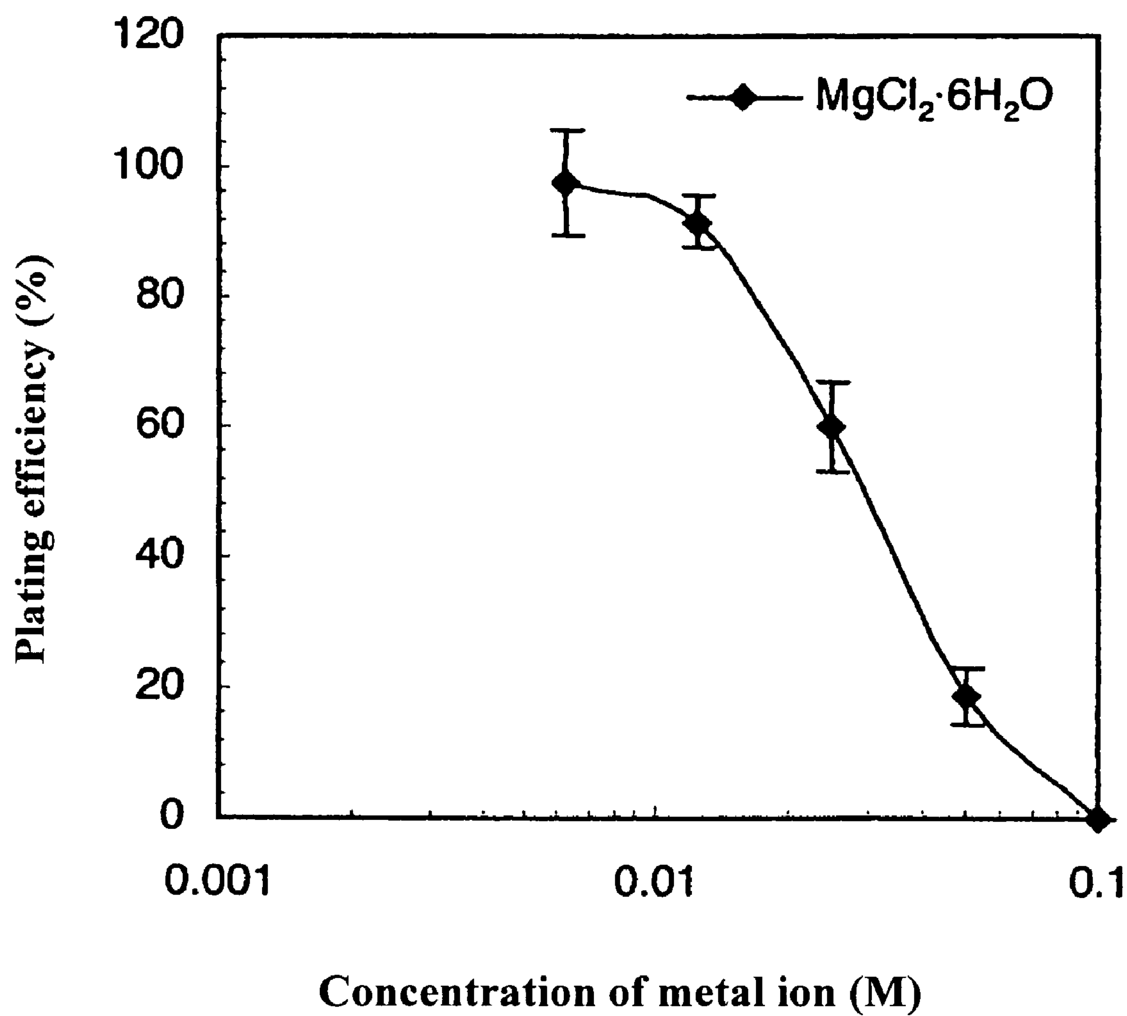
FIG. 5 is a graph illustrating results of cytotoxicity test of a magnesium chloride solution.

On the other hand, the cytotoxicity evaluation of a solution of 1M magnesium chloride hexa hydrate was performed according to Japanese pharmacopoeia using a murine fibroblast L929, and the result is shown in FIG. 5.

As a result, it was clarified that the concentration at which the magnesium ion inhibits the cell growth was equal to or more than 0.01 M (=243.1 mg/L).

This value is 4 to 10 times higher concentration than the amount of the released ion estimated as above. Accordingly, it may be understood that, for example, a stent of the present invention containing pure magnesium with the average grain size of 5 μm giving a large degradation speed does not have toxicity to a living body during degradation in the living body.

The cytotoxicity of the salts of Al, Y, Li, and In has been investigated among the added elements used for Example 4 (J. Biomed. Mater. Res. vol. 39, 331-340, 1998).

It has bee reported that the concentration ($IC_{50}$) that inhibit the proliferation of the murine fibroblast L929 by 50% gives 0.0132 M for LiCl; 4.18 mM for $Al(NO_3)_3$; 0.254 mM for $YCl_3$; and 0.145 mM for $InCl_4$.

For In having the highest cytotoxicity among these elements, the released amount was estimated using a magnesium alloy containing 0.3 atomic % of In as an example.

When it is assumed that In will be released at the same ratio as the alloy composition, the released amount of In on the 1st day, that gave the highest release, is 2 μM for the above-described average stent as an example. This value is approximately 1/50 of $IC_{50}$ of In (0.145 mM=100 μm).

Accordingly, it was confirmed that even in the alloys containing In, taking the shape of the device and of the degradation speed of the alloy into consideration enables to use them as biodegradable alloys for medical application.

INDUSTRIAL APPLICABILITY

The present invention provides biodegradable alloys for medical application comprising magnesium, that is one of the trace essential elements for the human being, and an alloy thereof, which will degrade and absorbed in the body after use.

Furthermore, the control of the composition and grain size of the material can control its degradation speed in the living body while realizing desired mechanical properties such as strength, work hardening and ductility for each device.

Since the magnesium alloys can realize desired mechanical properties such as strength, work hardening, and ductility as well as degradation speeds with a simply composition such as adding only one kind of alloying element, more precise management of the degradation speed, influence on the living body, etc. can be attained.

Use of this magnesium-based biodegradable metallic materials enables the removal of the metallic devices having become unnecessary from the inside of the body without various burdens to patients, such as operation.

Furthermore, biodegradable materials for medical application currently available are polymeric and ceramic materials, which should not be applied as medical devices required superior mechanical properties. The magnesium-based biodegradable metallic materials according to the present invention, however, can realize, for example, implants for orthopedics, such as biodegradable fracture fixation systems, etc.

Medical treatment expenses are increasing every year by Europeanization of eating habits and by an arrival of ultra-aged society, and the demands for biodegradable materials for medical application will be expected to increase easily.

The magnesium-based biodegradable metallic materials of the present invention, for example, can solve the problems of stent restenosis, make removal of bone plates, etc. by reoperation unnecessary, and moreover, the present invention can provide magnesium-based biodegradable metallic materials also applicable to regenerative medicine of hard tissues where loads are to be applied, such as bone, tooth, etc. which has been impossible so far.

Contribution to the reduction of medical treatment expenses and to the improvement in QOL will be expected.

The invention claimed is:

1. An implant device for medical application being used by being implanted in a living body, comprising a principal part formed by a magnesium-based biodegradable metallic material consisting of (i) Mg at a concentration equal to or more than 93.5 atomic %, (ii) one element having a larger metallic radius than that of magnesium, as a secondary composition, at a concentration equal to or less than 1/3 of its solubility limit to magnesium and its concentration unevenly distributed at a grain boundary is controlled to be a concentration equal to or more than 1.5 times of an average concentration in the grain, and (iii) inevitable impurities at a concentration equal to or less than 0.05 atomic %, and no precipitates or intermetallic compounds, and its average grain size is equal to or less than 1/4 of a minimum part of a structural component.

2. The implant device for medical application according to claim 1, wherein the magnesium-based biodegradable metallic material includes the secondary composition at a concentration equal to or less than 1/4 of its solid solubility limit to magnesium.

3. The implant device for medical application according to claim 1, wherein the magnesium-based biodegradable metallic material includes any one element among Ce, Pr, La, Th, Rb, Ho, Tm, Er, Lu, Nd, Ca, Yb, Y, Gd, Dy, Sc, and In as the secondary composition.

4. An implant device for medical application being used by being implanted in a living body, comprising a principal part formed by a magnesium-based biodegradable metallic material consisting of (i) Mg at a concentration equal to or more than 93.5% atomic %, (ii) one element having a smaller metallic radius than that of magnesium, as a secondary composition, at a concentration equal to or less than 1/3 of its solubility limit to magnesium and its concentration unevenly distributed at a grain boundary is controlled to be a concentration equal to or more than 1.2 times of an average concentration in the grain, and (iii) inevitable impurities at a concentration equal to or less than 0.05 atomic %, and no precipitates or intermetallic compounds, and its average grain size is equal to or less than 1/4 of a minimum part of a structural component.

5. The implant device for medical application according to claim 4, wherein the magnesium-based biodegradable metallic material includes the secondary component at a concentration equal to or less than 1/4 of its solubility limit to magnesium.

6. The implant device for medical application according to claim 4, wherein the magnesium-based biodegradable metallic material includes any one element among Au, Ir, Pd, Mn, Co, Ga, Ag, Al, Zn, Zr, Bi, Pu and Li as a secondary composition.

7. The implant device for medical application according to claim 1, wherein a structural component is formed of the magnesium-based biodegradable metallic material having a shape of a pipe or a pipe-like shape.

8. The implant device for medical application according to claim 7, wherein the degradation of the structural component formed from the magnesium-based biodegradable metallic material in the living body is designed to complete in a period of 5 days to 6 months after being implanted.

9. The implant device for medical application according to claim 8, wherein the degradation of the structural component formed from the magnesium-based biodegradable metallic material in the living body is designed to complete in a period of one week to 12 weeks after being implanted.

10. The implant device for medical application according to claim 7, wherein the device is any one of a coil, a shield, a stent, a wire knitted fabric, a clip, or a plug.

11. The implant device for medical application according to claim 7, wherein the implant device for medical application is an implant for orthopedics.

12. The implant device for medical application according to claim 11, wherein its degradation in the living body is completed in a period of 6 months to 5 years after being implanted.

13. The implant device for medical application according to claim 11, wherein its degradation in the living body is completed in a period of 8 months to 3 years after being implanted.

* * * * *